United States Patent [19]
Wolf

[11] Patent Number: 6,153,873
[45] Date of Patent: Nov. 28, 2000

[54] OPTICAL PROBE HAVING AN IMAGING APPARATUS

[75] Inventor: William Edward Wolf, Chesapeake City, Md.

[73] Assignee: E. I. duPont de Numours and Company, Wilmington, Del.

[21] Appl. No.: 09/081,989

[22] Filed: May 20, 1998

[51] Int. Cl.[7] .......................... G01N 21/00; G01N 15/02
[52] U.S. Cl. ...................... 250/208.1; 250/573; 250/216
[58] Field of Search .................................. 250/573, 576, 250/208.1, 574, 575, 216; 348/79, 89, 91; 356/335, 336, 337, 338, 339, 340, 343; 382/168, 110

[56] References Cited

U.S. PATENT DOCUMENTS

| | | | |
|---|---|---|---|
| 4,095,775 | 6/1978 | Hotham | 356/102 |
| 4,121,247 | 10/1978 | Henry | 358/107 |
| 4,136,950 | 1/1979 | Labrum et al. | 356/28 |
| 4,177,482 | 12/1979 | Henry | 358/93 |
| 4,245,909 | 1/1981 | Loos | 356/336 |
| 4,492,467 | 1/1985 | Drain et al. | 356/336 |
| 4,529,306 | 7/1985 | Kilham et al. | 356/237 |
| 5,377,005 | 12/1994 | Meyer | 356/335 |
| 5,731,894 | 3/1998 | Gross | 356/237 |
| 5,798,829 | 8/1998 | Vaez-Iravani | 359/386 |

*Primary Examiner*—John R. Lee
*Attorney, Agent, or Firm*—George M. Medwick

[57] ABSTRACT

An imaging apparatus includes a collection of optical elements arranged in a predetermined sequence and cooperable to define a dark-field optical arrangement and a bright-field optical arrangement. The dark-field optical arrangement and a bright-field optical arrangement may be defined along the same or different optical path(s). At least one of the optical elements is operative to enable at least one of the dark field or the bright-field optical arrangements. In a first embodiment said one optical element is movable from a first to a second position to enable either the dark-field or the bright-field optical arrangement. In a second embodiment said one optical element is operable to enable simultaneously both the dark-field and the bright-field optical arrangements. Both opaque objects and phase objects in a fluid stream are able to be detected and quantified.

20 Claims, 14 Drawing Sheets

OPTICAL PROBE HAVING AN IMAGING APPARATUS

BACKGROUND OF THE INVENTION

1. Field of the Invention

The present invention relates to an imaging apparatus capable of operating either simultaneously or alternately as a bright-field optical arrangement and/or a dark-field optical arrangement, and to an optical probe having the imaging apparatus included therein.

2. Description of the Prior Art

Contaminants in liquid feedstock streams have long been a major problem within the chemical manufacturing industry. Such contaminants may be in the form of either opaque objects, such as solid particulates, or "phase objects", such as gels and transparent inclusions. Phase objects are a particular problem in polymer manufacturing processes. Phase objects do not typically scatter or absorb light and are thus difficult to see in a polymer stream. However, a phase object usually has an index of refraction that is slightly different from the primary polymer stream due to a difference in molecular weight which causes light which passes through the phase object to refract or change direction.

A prior art commercial system, such as that manufactured by Flow Vision, Inc., of Morgantown, Pa., uses bright-field optics to effectively detect opaque objects in a fluid stream. This system is relatively insensitive to phase objects.

The optical principles underlying a bright-field optical arrangement may be understood from FIG. 1. In the bright-field optical system in FIG. 1, viewing from left to right along an optical axis A are a light source S, which can be a light guide or a lamp, a plate having an aperture $S_A$, a collimating lens L1, and the material or medium M under test. At the right are the detection optics, comprising a pair of imaging lenses L2 and L3, and an output image plane P. A photodetector, such as a charge coupled device (CCD) array camera, can be positioned at the output image plane. Alternately, a coherent fiber optic bundle faceplate can be positioned at the output image plane to convey light to a distant photodetector.

Light passing through the material or medium M under test is imaged at the output image plane P and thus permitted to impinge on the photodetector. Opaque objects in the material M block light from passing therethrough, and thus cause corresponding dark regions at the image plane, making such objects readily detectable. Hence, a reduction of photons at the photodetector indicates the presence of something in the field of view that is absorbing or blocking the light passing through the medium.

Phase objects can be optically detected using dark-field detection techniques, such as Schlieren methods, which offer significant advantages over bright-field imaging. A description of Schlieren methods may be found in Jenkins, F. A. and White, H. E., *Fundamentals of Optics*, 4th Edition, McGraw-Hill, New York, 1976, p. 602 and in Vasil'ev, L. A., *Schlieren Methods*, Halstead Press, New York, 1971. U.S. Pat. No. 4,121,247 (Henry) discloses a Schlieren dark-field detection system. Dark-field detection techniques are typically unable to detect opaque objects.

The optical principles underlying a dark-field optical arrangement may be understood from FIG. 2. In a homogeneous transparent medium (i. e., one that does not vary in its index of refraction) light travels in a straight line. A transparent object or region in the medium M having an index of refraction slightly different from the medium will cause light passing though it to change direction slightly. Phase objects, although usually transparent, frequently have a slightly different index of refraction from the surrounding polymer stream. When a light ray passes through a phase object, the ray direction vector is refracted according to Snell's law. Even a very small change in the index of refraction can cause a surprisingly large change in the direction of an incident light ray. This change in the direction of light propagation provides a mechanism for detecting phase objects.

FIG. 2 illustrates a dark-field telecentric optical system wherein light rays pass through a material or medium under test parallel to an optical axis A. Viewing from left to right along the optical axis A are a light source S, which can be a light guide or a lamp, a plate having an aperture $S_A$, a collimating lens L1, and the material or medium under test M. At the right are the detection optics, comprising a lens L2, a beam stop B, which blocks the undisturbed light rays, an imaging lens L3, and an output image plane P. A photodetector, as a charge coupled device (CCD) array camera, can be positioned at the output image plane. Alternately, a coherent fiber optic bundle faceplate can be positioned at the output image plane to convey light to a distant photodetector.

The undisturbed rays are blocked by the beam stop B, and only refracted rays R are imaged in the output image plane P and thus permitted to impinge on the photodetector. Hence, the presence of photons at the photodetector indicates the presence of something in the field of view that is changing the direction of the light in the medium. Phase objects and related artifacts appear as bright objects in a dark background at the image plane, making them readily detectable. However, because diffraction can also cause this same effect, such a system is sensitive to very small solid objects that diffract light, as well as refracting artifacts.

Although FIG. 2 illustrates a dark-field telecentric optical system it should be understood that a dark-field focused beam optical system, wherein the light rays converge as they pass through the object plane, may be used. Again, when the optical path through the test material contains no artifacts that disturb the light transmission all light rays are blocked by the stop B and the output image is dark.

In view of the foregoing it is believed advantageous to provide an optical probe having an imaging apparatus capable of operating either simultaneously or alternately as a bright-field optical arrangement and/or a dark-field optical arrangement. It is also believed advantageous to provide an optical probe able to operate within the hostile environment of a complex chemical process.

SUMMARY OF THE INVENTION

The present invention relates to an imaging apparatus that includes a collection of optical elements arranged in a predetermined sequence. The optical elements are cooperable to define a dark-field optical arrangement and a bright-field optical arrangement. The dark-field optical arrangement and a bright-field optical arrangement may be defined along the same or different optical path(s). In accordance with the present invention at least one of the optical elements is operative to enable at least one of the dark-field or the bright-field optical arrangements. In a first embodiment said one optical element is movable from a first to a second position to enable either the dark-field or the bright-field optical arrangement. In a second embodiment said one optical element is operable to enable simultaneously both the dark-field and the bright-field optical arrangements. The apparatus of the present invention is thus capable of detecting and quantifying the concentration of both opaque objects and phase objects in a fluid stream.

BRIEF DESCRIPTION OF THE FIGURES

The invention will be more fully understood from the following detailed description taken in connection with the accompanying drawings, which form a part of this application and in which.

DETAILED DESCRIPTION OF THE INVENTION

Figure 1:
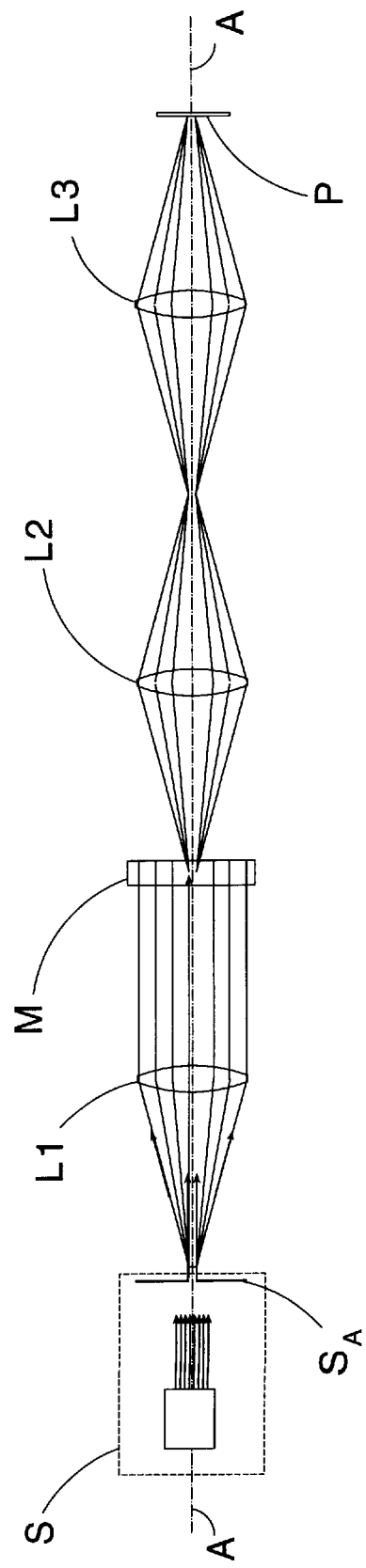
FIGS 1 and 2 are ray trace diagrams which illustrate, respectively, the optical principles underlying a bright-field optical arrangement and a dark-field optical arrangement.
Figure 2:
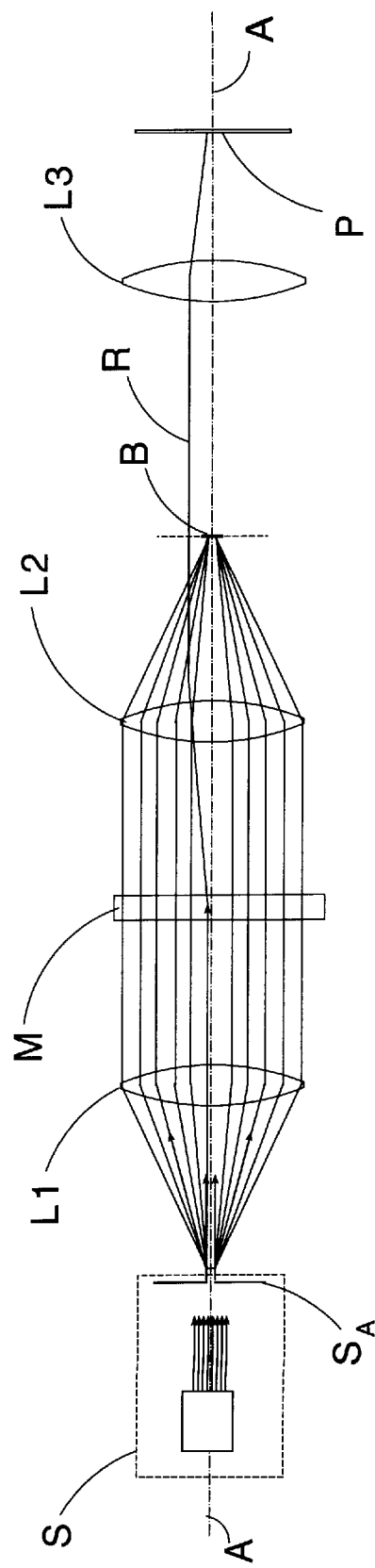

Throughout the following detailed description similar reference numerals refer the similar elements in all figures of the drawings.

Figure 3:
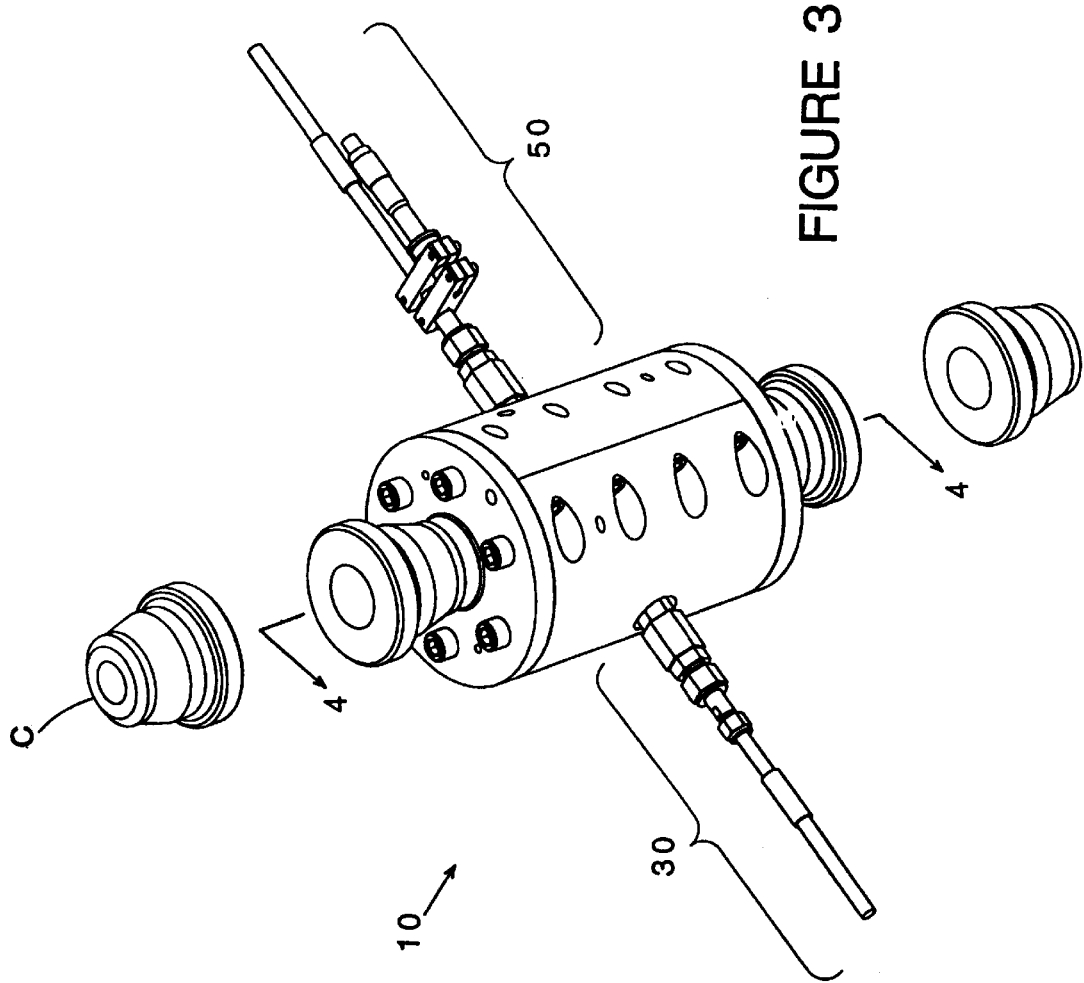
FIG. 3 is a perspective view of the optical probe of the present invention installed in a typical flow cell.

FIG. 3 shows a probe generally indicated by the reference character 10 having an imaging apparatus in accordance with the present invention therein. The imaging apparatus comprises an optical source assembly 30 and an optical detector assembly 50. The probe 10 may include or be cooperably associated with a flow cell 20.

The flow cell 20 comprises a housing 22 (FIG. 4) having a channel 24 therethrough. The channel 24 has an inlet region 24I, a viewing region 24V and an outlet region 24R defined sequentially along a central axis 24A extending therethrough. The flow cell 20 is adapted to be connected at inlet 24I and outlet 24R within a fluid transport conduit C (FIG. 3) such that a stream F having entrained objects therein may pass through the channel 24. The channel 24 is configured with the appropriate geometry to conduct the stream F through the viewing region 24V and to provide the proper optical path length consistent with the fluid characteristics.

Figure 4:
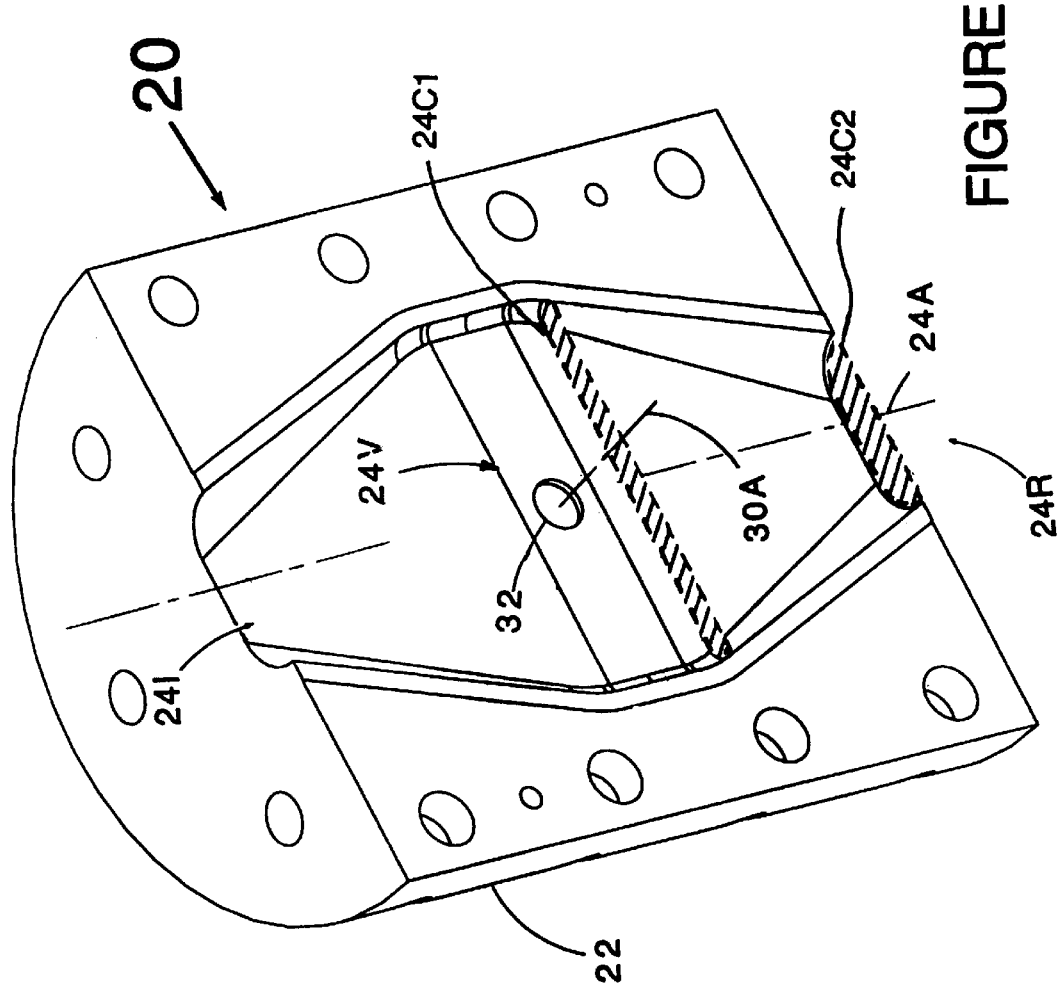
FIG. 4 is a cutaway view taken along view lines 4—4 of FIG. 3 showing interior details of the flow cell.

The constructional details of the preferred flow cell 20 are best illustrated in a cutaway pictorial view in FIG. 4. In this figure the central axis 24A of the flow channel 24, the window 32 of source assembly 30, and the optical axis 30A of the source assembly 30 are shown. It is preferred that the cross-sectional area of the channel 24 in any plane perpendicular to the axis 24A through the channel is substantially constant. This relationship of cross-sectional areas is illustrated by representative hatched areas 24C1, 24C2. This arrangement provides a short optical path length through the viewing region 24V without presenting an unduly large pressure drop to the fluid stream F.

Generally speaking the optical source assembly 30 supplies light to the viewing region 24V. The optical detector assembly 50 collects and detects light passing through the viewing region 24V. The optical source assembly 30 includes some form of aperture, while the optical detector assembly 50 includes some form of a spatial filter. To implement a dark-field optical arrangement it should be appreciated that the spatial filter of the detector assembly must be the optical inverse of the aperture of the optical source assembly. The optical density profile of the aperture may take any predetermined shape. Thus, the optical density profile of the spatial filter is the inverse of the optical density profile of the aperture.

Figure 5A:
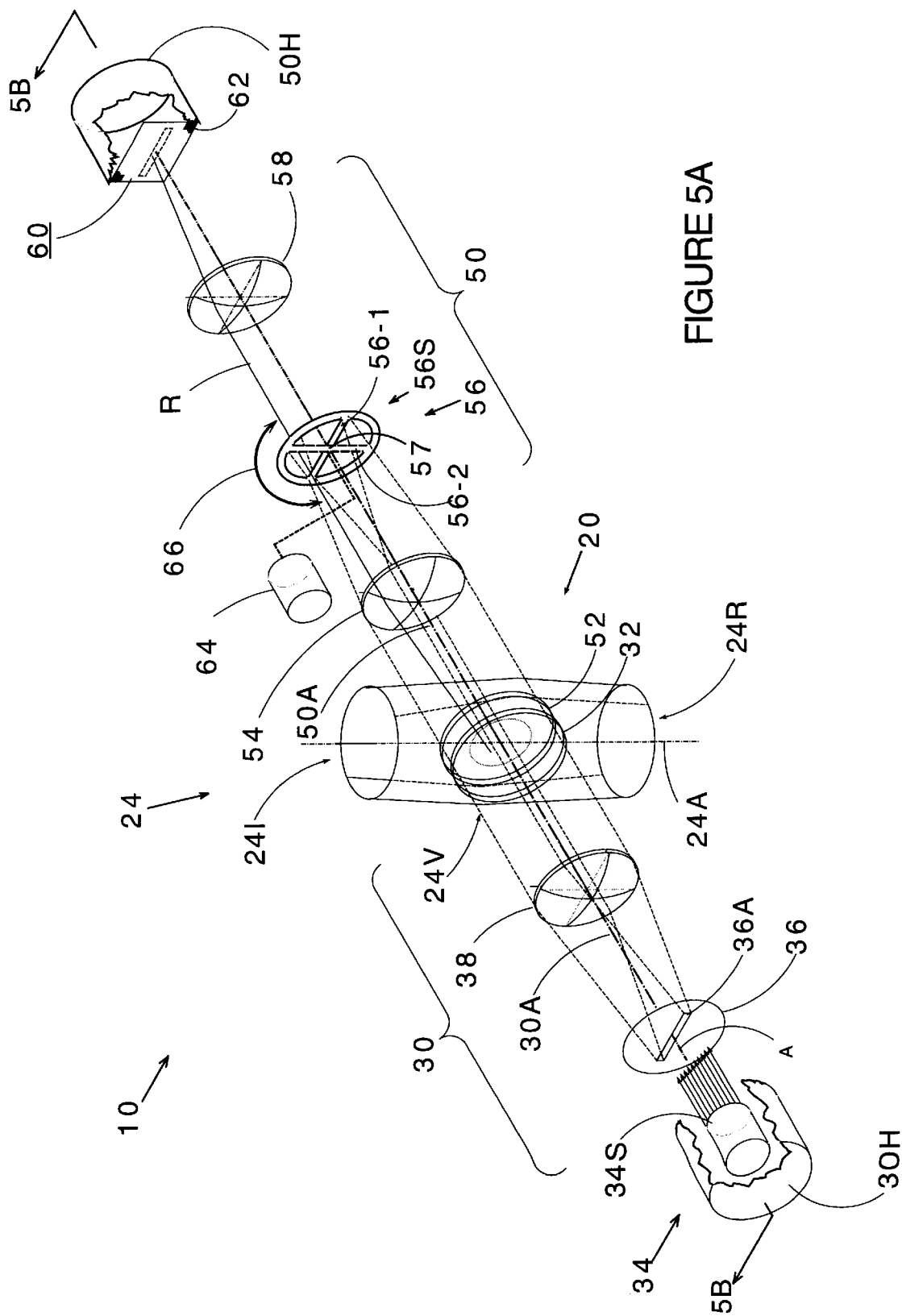
FIG. 5A is an optical schematic diagram of a first embodiment the present invention having a rotatably movable optical element to enable either the dark-field or the bright-field imaging arrangement, with the housings broken away for clarity of illustration.
Figure 5B:
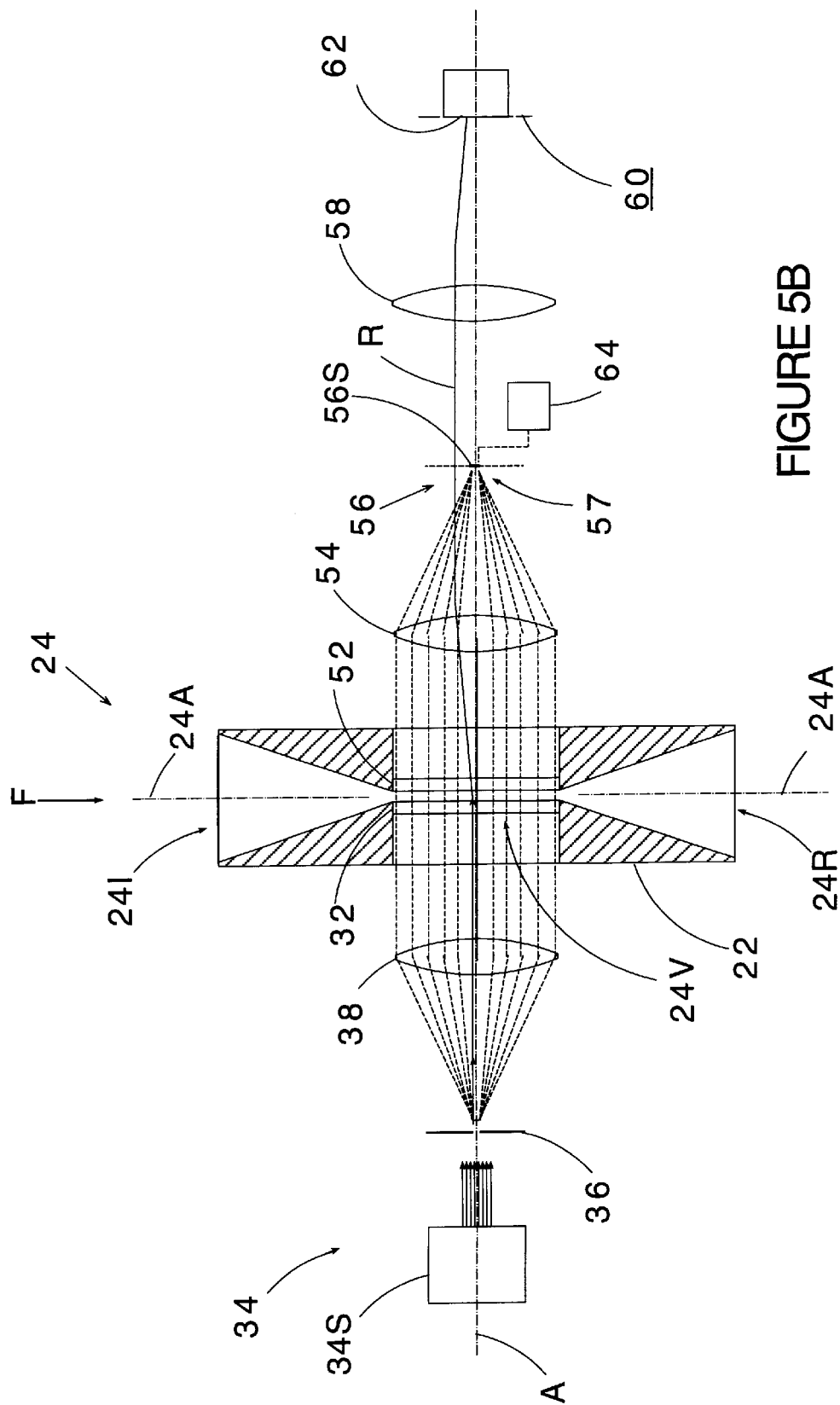
FIG. 5B is a sectional view taken along view lines 5B—5B of FIG. 5A.

As seen in FIG. 5A the optical source assembly 30 and the optical detector assembly 50 are housed in ruggedized tubular housings 30H, 50H, capable of withstanding the temperature and pressure of the fluid stream F. The housings 30H, 50H terminate at windows 32, 52 respectively. The windows 32, 52 may be conveniently mounted within the walls of the flow cell 20 to define the viewing region 24V as illustrated in FIGS. 5A, 5B. Alternatively the windows 32, 52 may be mounted at the ends of the housings 30H, 50H and thus form part of the optical source assembly 30 and the optical detector assembly 50, respectively. The source assembly 30 and the detector assembly 50 each have a respective optical axis 30A, 50A. In a typical configuration the source assembly 30 and the detector assembly 50 are positioned with their axes 30A and 50A on a common axis A (FIG. 5A).

Mounted within the tubular housing 30H of the optical source assembly 30 are a light source assembly 34 and a lens arrangement 38. The light source assembly 34 has a light source 34S and a plate 36. The plate 36 is formed from an optically opaque material and has a beam-shaping opening cut therein to define an aperture 36A (FIG. 5A). Alternatively, the aperture in the light source assembly 34 may be configured from a selectably metallized transparent member. The light source 34S may be mounted outside the housing 30H and may communicate therewith by an optical conduit such as a fiber optic light pipe (not shown).

The light source 34S may be implemented using a continuous light source or a pulsed light source. A continuous light source is preferably implemented using a servo-controlled, regulated constant intensity lamp. Suitable for use as such a continuous source is the commercially available intensity-controlled continuous light source such as a Model IT-3900 made by Illumination Technology, Inc. of East Syracuse, N.Y. This light source is preferred since it permits a constant light output which may be maintained over the lifetime of the lamp used in the light source. Typically a 150 watt lamp has been found sufficient for most clear fluids or polymers. The light source 34S in the form of a pulsed light source may be implemented using a gas discharge strobe lamp, a pulsed light emitting diode, or a pulsed laser.

The beam of light from the aperture 36A is projected by the lens arrangement 38 through the window 32 and focused into a portion of the viewing region 24V of the channel to illuminate the fluid stream F therein.

FIGS. 5A and 5B show a telecentric optical system wherein the detector assembly 50 is in accordance with a first embodiment of the present invention. Mounted within the tubular housing 50H of the detector assembly 50 are a first lens arrangement 54, an optical element 56, and a second lens arrangement 58. The optical element 56 is a spatial filter fabricated from an optically opaque material to form a beam-blocking member which is the optical inverse of, and which corresponds in size and shape to, the aperture 36A. Alternatively, the spatial filter 56 may be configured from a selectably metallized transparent member.

The first lens arrangement 54 focuses the illuminated portion of the viewing region 24V onto the spatial filter 56 to create a spatially filtered image of the viewing region. The second lens arrangement 58 focuses the spatially filtered image of the viewing region onto an image plane 60. A photodetector 62 may be mounted within the housing 50H to lie on the image plane 60 within the housing 50H (as shown). Alternatively, the photodetector 62 may be optically coupled to the image plane 60, as by an optical image transmitting conduit such as an image transmitting fiber optic light pipe (not shown).

In both the first and second embodiments of the invention the aperture plate 36 and the spatial filter 56 comprise optical elements that cooperate to define both a dark-field imaging arrangement and a bright-field imaging arrangement. In accordance with the present invention at least one of these optical elements is operative to enable at least one of these imaging arrangements. As will be developed the imaging arrangements may be enabled either individually or simultaneously.

In a first embodiment one of these optical elements is movable from a first to a second position with respect to the other element to enable either the dark-field or the bright-field imaging arrangement. As seen in FIGS. 5A and 5B a first version of the first embodiment may be implemented by rotatably moving the spatial filter 56 with respect to the aperture 36A in the aperture plate 36 to misalign these members. To this end an actuator 64 is operatively associated with the spatial filter 56 for rotationally moving the same. The actuator 64 may be implemented by using a linear solenoid which is operatively connected to a rotation mechanism via a wire/pulley arrangement. The spatial filter 56 is mounted to the rotation mechanism. Alternately, the spatial filter 56 may be mounted on a rotary solenoid.

As seen in FIG. 5A the aperture 36A preferably takes the form of a elongated transparent slit and the spatial filter 56 takes the form of an opaque line beam stop 56S. When in the first position (as shown by the solid line representation of spatial filter designated 56-1, FIG. 5A) the beam stop 56S and the aperture 36A are substantially rotationally aligned. When in the second position (as shown by the dotted line representation of spatial filter designated 56-2, FIG. 5A) the beam stop 56S and the aperture 36A are substantially misaligned to define a predetermined azimuthal angle with respect to each other. The azimuthal angle between the aperture and the spatial filter in the second position is typically in the range from about thirty (30) degrees to about one hundred fifty (150) degrees, with an angle of about ninety (90) degrees being preferred. In the first position 56-1 only light refracted or diffracted by objects in the fluid stream F moving through the viewing region 24V is imaged onto the image plane 60. Light which is not refracted or diffracted is substantially attenuated by the beam stop 56S so that objects which only refract or diffract light are detected. When in the second position 56-2 substantially all the light illuminating the viewing region 24V is imaged onto the image plane 60 so that objects which absorb light are detected.

Although the aperture plate 36 is shown to be fixed and the beam stop 56S is shown to be the rotationally movable optical element, it may be appreciated by one skilled in the optical detection art that the actuator 64 could be operatively associated with the aperture plate 36 for positioning the aperture 36A into the predetermined first and second positions with respect to the beam stop 56S. Further, the actuator 64 could be operatively associated with both the aperture plate 36 and the beam stop 56S to achieve the predetermined first and second relative positions of these elements.

Figure 6:
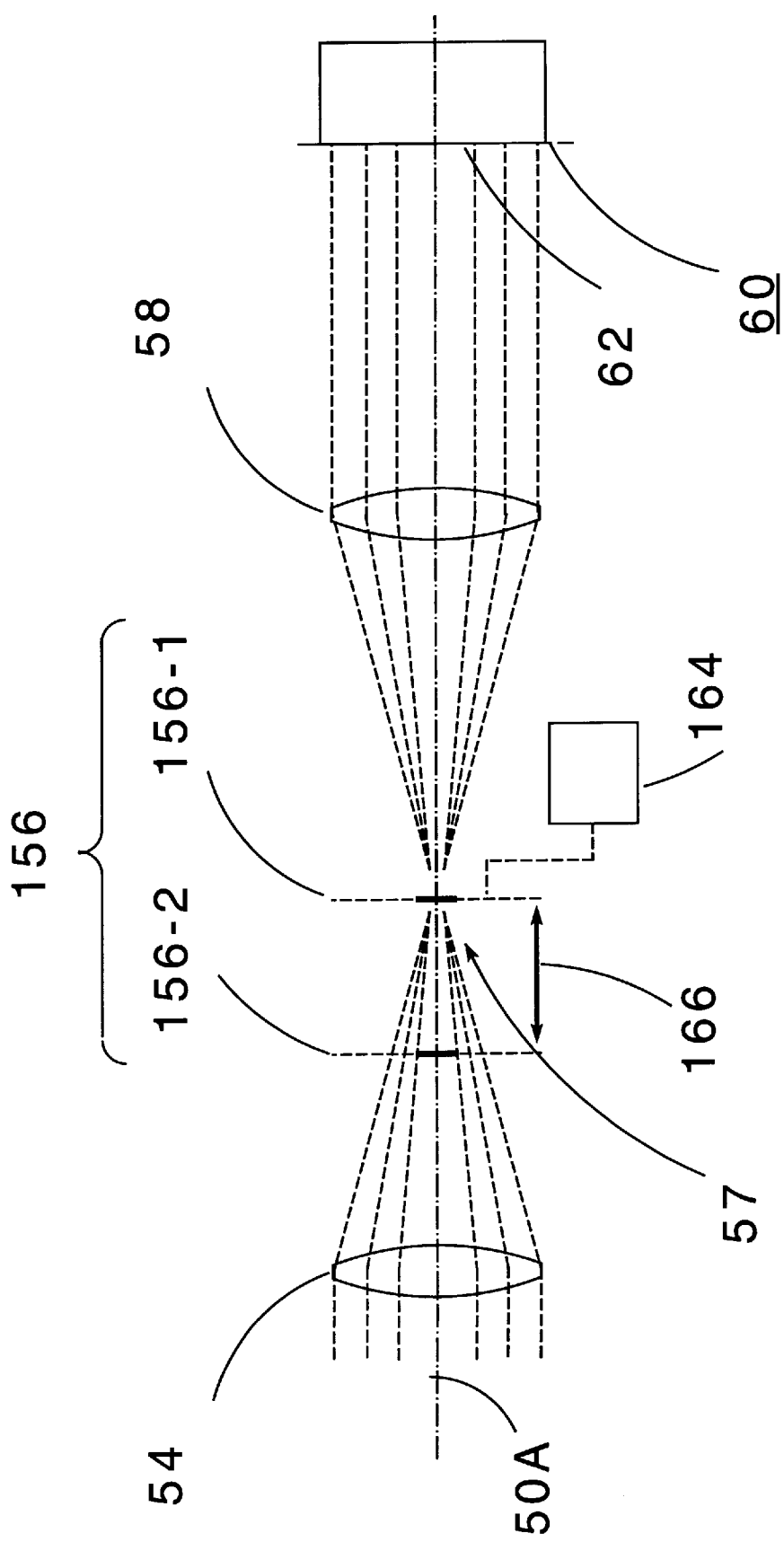
FIG. 6 shows a second version of the first embodiment of the present invention having an optical element displacable along the optical path.
Figure 7:
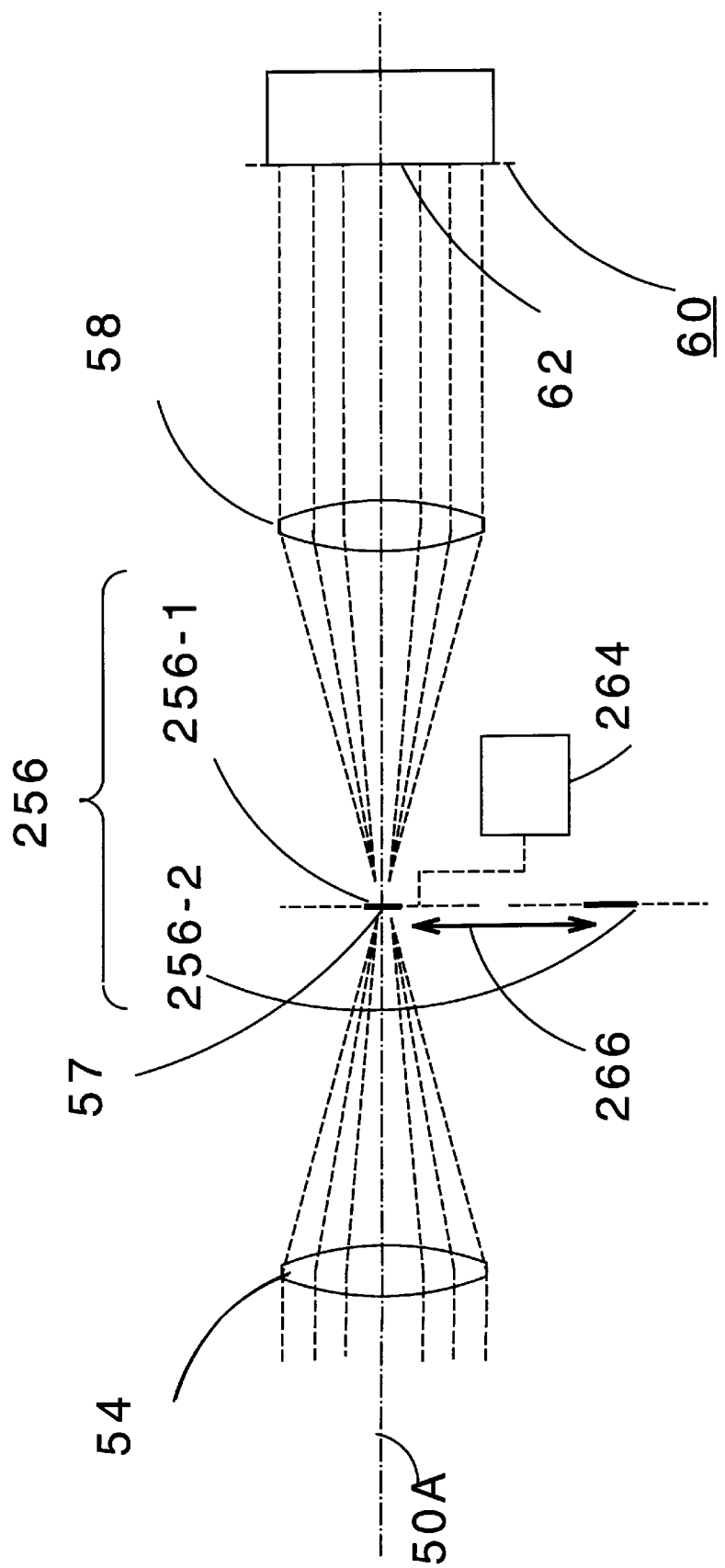
FIG. 7 shows a third version of the first embodiment of the present invention having an optical element displacable transversely into and from the optical path.

FIGS. 6 and 7 illustrate alternate versions of the first embodiment wherein the movable optical element is the beam stop 156S or 256S, respectively. In the version of FIG. 6 the movable beam stop 156S is axially displaced by the actuator 164 along the optical axis 50A in the direction of the arrow 166 from a first position 156-1 on the axis 50A at the focal point 57 of the lens arrangement 54 to second position 156-2 on the axis 50A away from the focal point 57. In the version of FIG. 7 the movable optical beam stop 256 is transversely displaced by the actuator 264 in the direction of the arrow 266 from a first position 256-1 located at the focal point 57 of the lens arrangement 54 to a second position 256-2 off the axis 50A away from the focal point 57. In either case, when in the second position, the beam stop 156S or 256S is thus translationally misaligned from the aperture 36A. Although the arrows 166 and 266 indicate rectilinear displacement, the optical element could move along any arbitrary paths and remain within the spirit of the invention.

It is again to be noted that, although beam stop 156S, 256S is respectively shown in FIGS. 6 and 7 to be the movable optical element, it may be appreciated that the actuator 64 could be operatively associated with the aperture plate 36 to move the same, thereby to shift the portion of the viewing region 24V being examined and to shift the focal point 57. Either of these is functionally equivalent to moving the beam stops 156S, 256S, as previously described. Further, the actuator 64 could be operatively associated with both the aperture plate 36 and the beam stops 156S, 256S.

Apparatus in accordance with the second embodiment of the invention includes an optical element 56 which receives light from the viewing region and directs and passes the light from the viewing region simultaneously to both the dark-field and bright-field imaging arrangements. The optical element 56 is again implemented as a spatial filter. In a preferred implementation of the second embodiment seen in FIGS. 8A and 8B the spatial filter takes the form of a reflective beam stop 56M, such as a mirrored line-shaped beam stop. Such a line-shaped beam stop is the optical inverse of the aperture 36A. As would be readily appreciated by one skilled in the art, the beam stop 56M may alternatively be implemented using a mirrored beam stop having a line-shaped aperture. It should be noted that the rendition of the spatial filter 156S, 56S, 256S and 56M has been exaggerated in scale in FIGS. 5B, 6, 7 and 8B, respectively, for clarity of illustration. It should be noted that, as shown in FIG. 8B, the optical element 56 also serves multiple additional functions. For the dark-field optical arrangement the optical element 56 functions as the beam stop, while for the bright-field optical arrangement the optical element 56 functions as an aperture. It should also be appreciated that the optical element 56 could be alternatively implemented using a beam splitter positioned between the lens 54 and focal point 57. Of course, in such an instance a separate beam stop and a separate aperture must be provided.

By positioning the reflective beam stop 56M within the housing 50H at the focal point 57 of the lens arrangement 54 and inclining the reflective beam stop 56R at an appropriate angle to the axis 50A those light rays whose direction through the viewing region 24V have not been changed by objects in the fluid F are reflected to a third lens arrangement 78. The third lens arrangement 78 focuses the spatially filtered image of the viewing region 24V onto a second image plane 80. A photodetector 82 may be mounted within the housing 50H to lie on the image plane 80. Again, as an alternative, the photodetector 82 may be optically coupled to the image plane 80, as by an optical image transmitting conduit such as an image transmitting fiber optic light pipe (not shown). This embodiment of the invention thus allows simultaneous detection of phase objects and opaque objects.

Although both embodiments of the present invention have been illustrated using a focused beam implementation, it should be understood that a telecentric beam implementation may be employed if desired.

Figure 10:
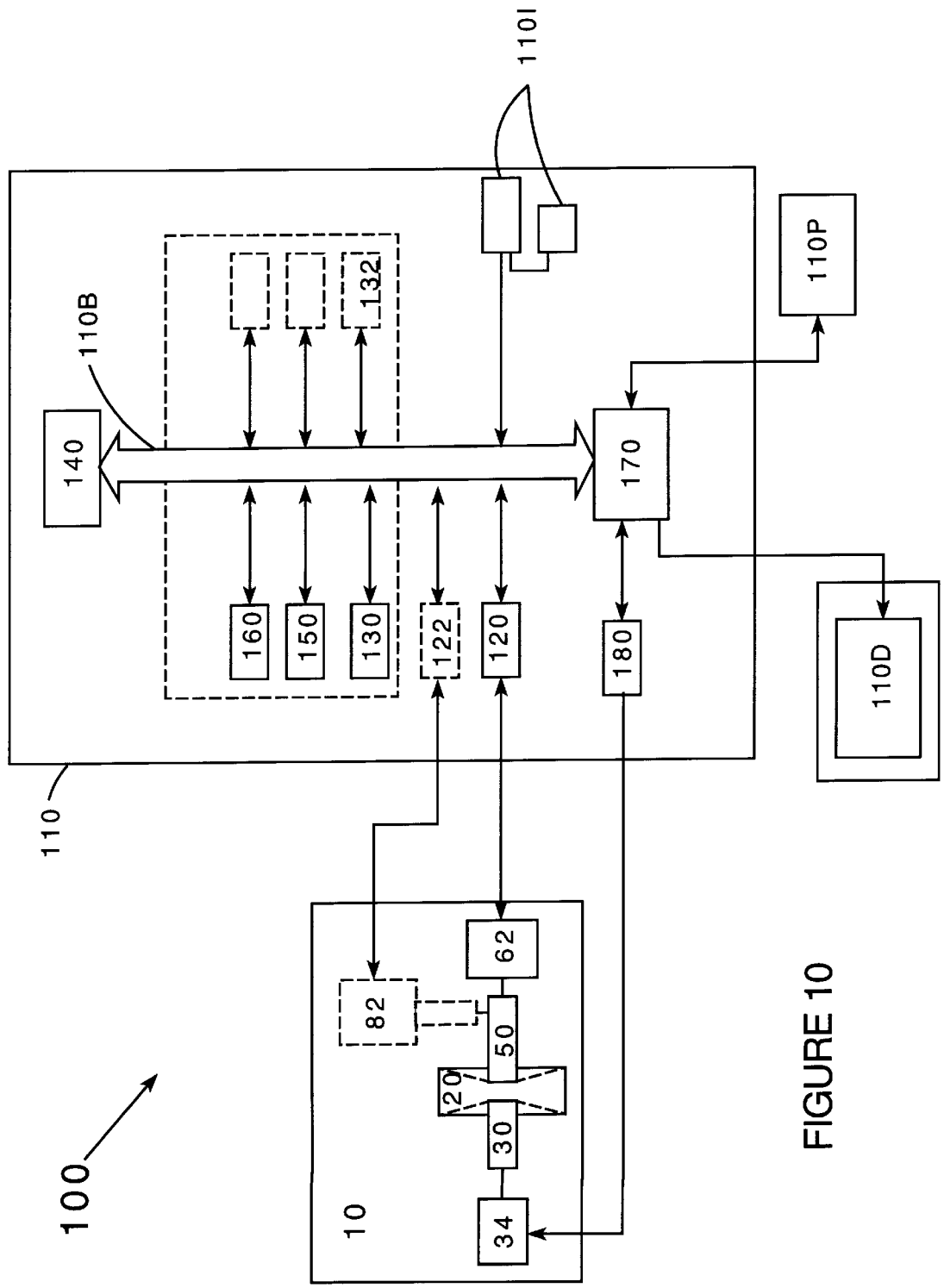
FIG. 10 is a block diagram of an optical detection system able to be used with the optical probe of the present invention.

The photodetector 62 (FIGS. 5A, 5B, 6 and 7) and the photodetector 82 (FIGS. 8A and 8B) are typically implemented using charge coupled device (CCD) array cameras which create electrical signals representative of the intensity of the detected light on a corresponding picture elements ("pixels") of the image plane and which transmit these images to the computer controlled image acquisition and processing system 100 (FIG. 10). The system 100 analyzes the images detected and converts the information about the detected objects into a form easily interpreted by production operators and process engineers.

Figure 8A:
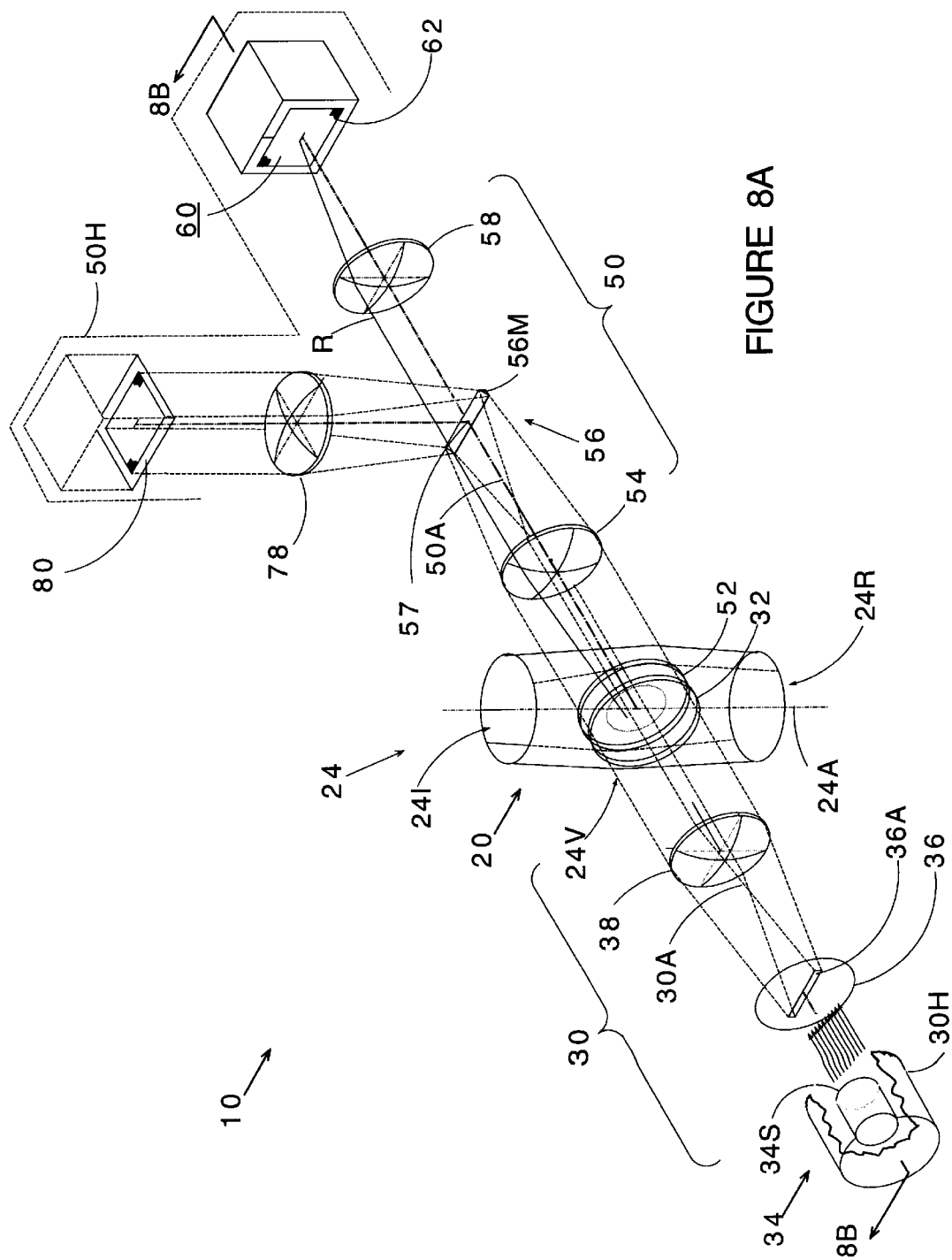
FIG. 8A is an optical schematic diagram of a second embodiment of the invention having an optical element operable to enable simultaneously both the dark-field and the bright-field imaging arrangements, with the housings broken away for clarity of illustration.
Figure 8B:
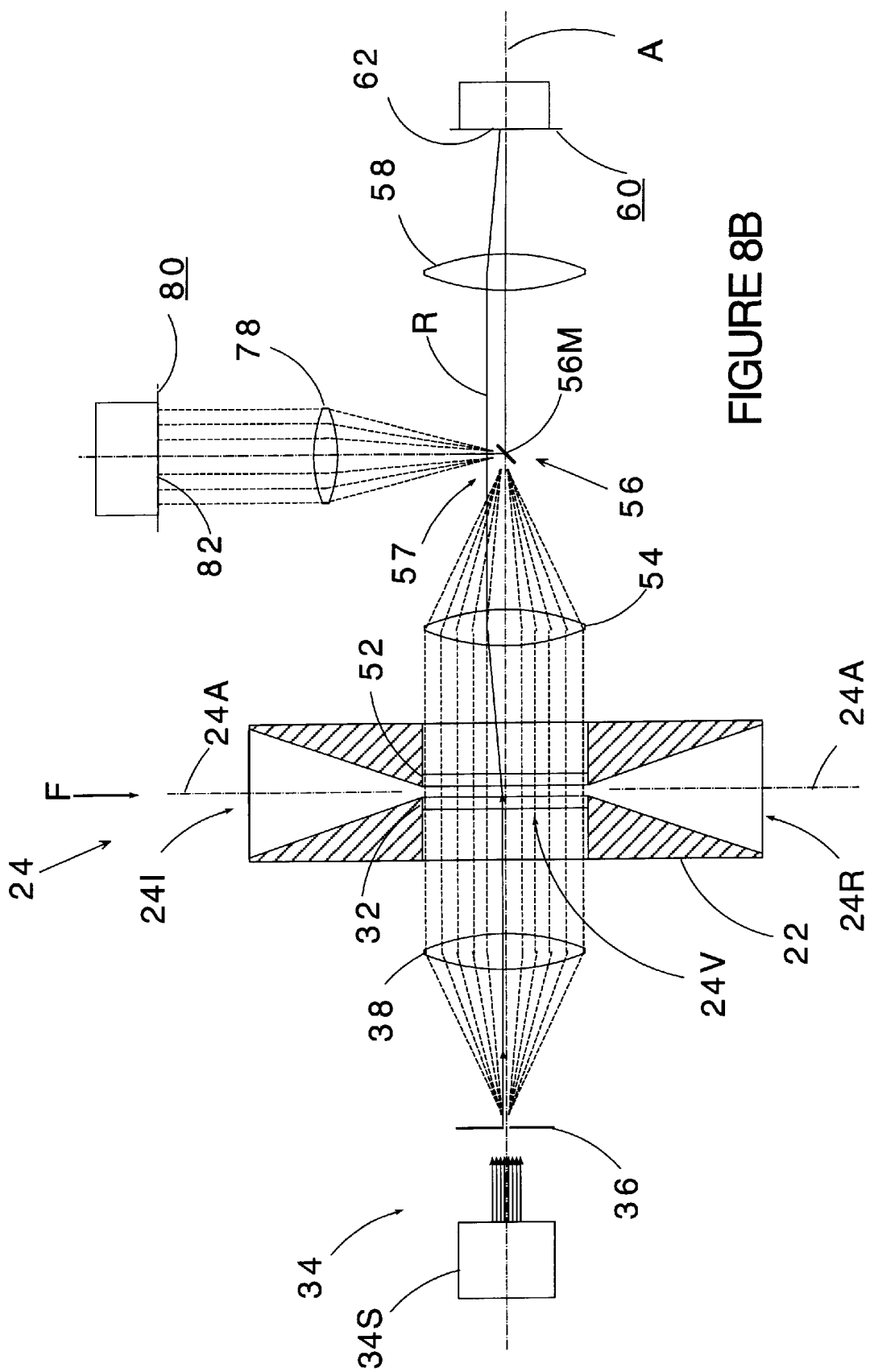
FIG. 8B is a sectional view taken along view lines 8B—8B of FIG. 8A.
Figure 9:
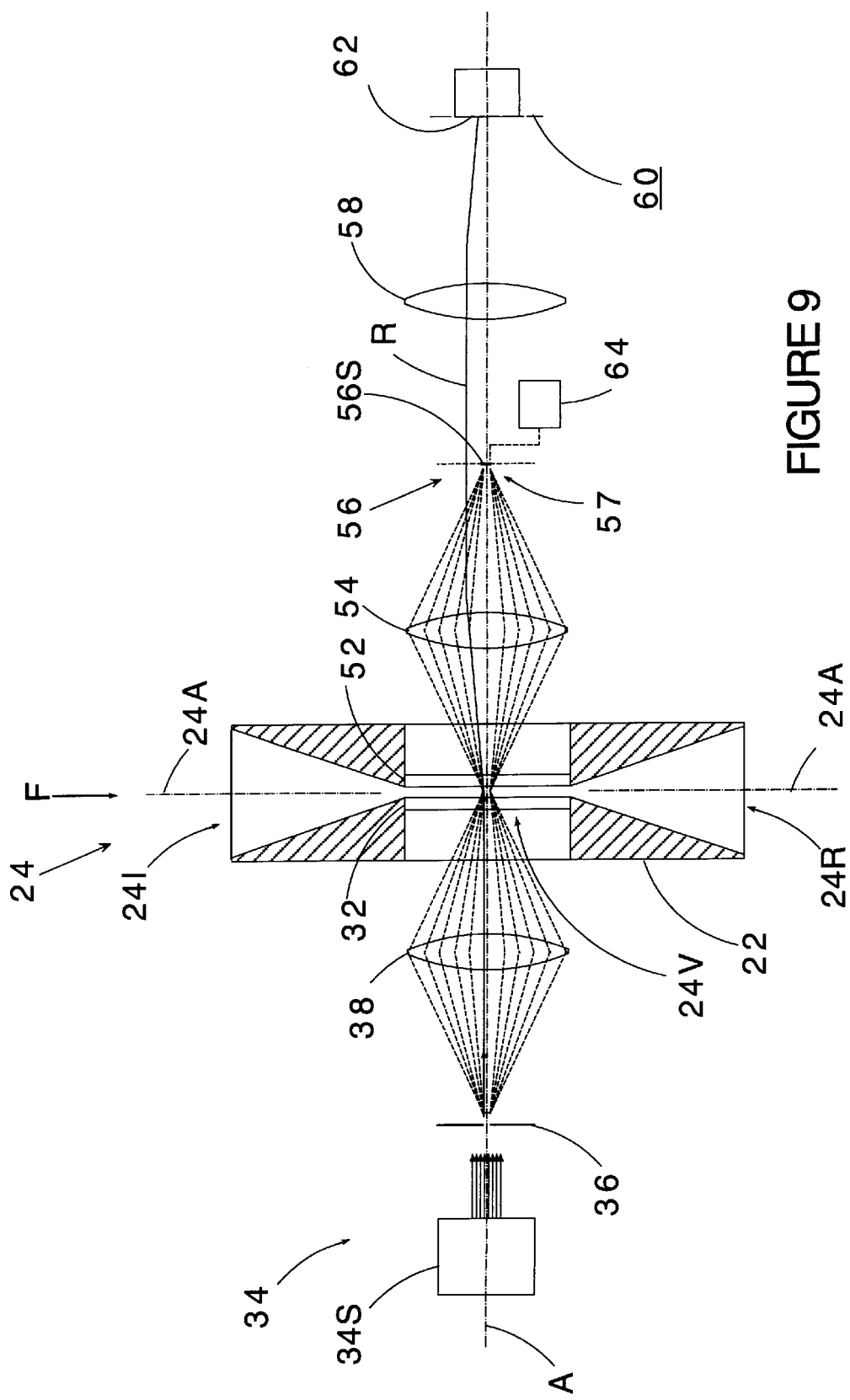
FIG. 9 is a sectional view, similar to a portion of FIGS 5B and 8B, showing the implementation of the present invention using a focused beam optical system.

It should be understood that although both the first embodiment of the present invention (as illustrated in FIGS. 5A, 5B, 6, 7) and the second embodiment of the present invention (as illustrated in FIGS. 8A and 8B) have been illustrated using a telecentric optical system, it should be understood that both embodiments of the present invention may be implemented using a focused beam optical system. FIG. 9 illustrates such a focused beam implementation. In a focused beam implementation the collimating lens 38 in the optical source assembly 30 (FIGS. 5A, 5B, and FIGS. 8A and 8B) is replaced by a focusing lens 39. Correspondingly the lens 54 in the optical detector assembly 50 (FIGS. 5A, 5B, 6, 7 and FIGS. 8A and 8B) is replaced by a lens 55. The focusing lens 39 causes the light rays to pass through the viewing region 24V in a converging manner. The lens 55 receives the light rays emerging from the viewing region and focuses them to the focal point 57. All other details of each version of each embodiment remain as described previously.

The block diagram in FIG. 10 shows the principle components of the system 100 arranged for a typical application. The computer controlled image acquisition and processing system 100 comprises a computer unit 110, such as an IBM compatible desktop computer, having an internal data bus 110B. Input peripherals, such as a keyboard or a mouse 110I are connected to he bus 110B. The bus 110B communicates with an analog to digital converter 120, an image memory 130, a central processor 140, a stored program memory 150, a results memory for storing image processor output results 160, an output port 170 and associated display 110D and printer 110P. The central processor 140 may also serve as an image processor under control of a program stored in program memory 150. A control interface 180 communicates with the output port 170 to control the light source 34, by either varying the intensity (in a continuous beam arrangement) or specifying the timing (in a pulsed arrangement). An additional analog to digital converter 122 and an associated image memory 132 may be optionally employed in the second embodiment described in conjunction with FIGS. 8A, 8B.

Figure 11:
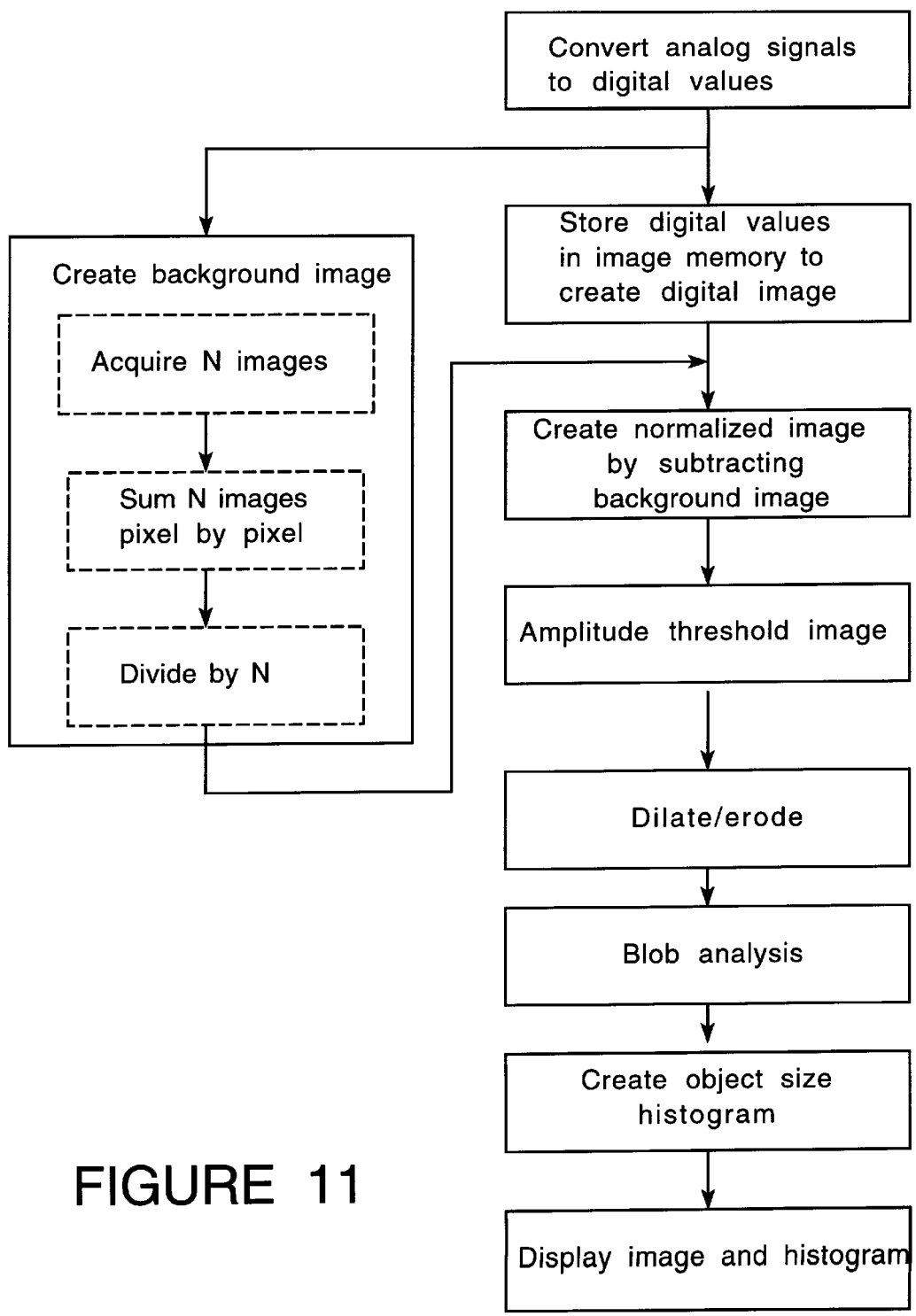
FIG. 11 is a block diagram illustrating the image processing method of the optical detection system of FIG. 10.

The block diagram in FIG. 11 illustrates the steps of an image processing method for detecting an object in a fluid stream. The method is useful with either embodiment of the present invention. Electrical signals from the photodetector 62 (and 82, for the optical arrangement of FIGS. 8A, 8B) are converted to digital values by the analog to digital converter 120 (and 122) to form a digital image of the viewing region 24V. The digital image of the viewing region is stored in the image memory 130 (and 132).

As the first step of the method a normalized image of the viewing region 24V is created. A normalized image is needed since the image transmitting fiber optic light pipe used in high temperature environments may add stationary artifacts to the acquired images. Other stationary artifacts in the optical system (such as an imperfection on one of the windows) may also add extraneous features that need to be removed from the images before they are subjected to the object threshold analysis (to be described below). Since it is difficult to remove the apparatus from a fluid stream once production has started it is advantageous to modify the background image dynamically to eliminate these artifacts as well as polymer artifacts that adhere to the windows 32, 52 during production.

The normalized image is created by the following steps. The image processor 100 acquires a plurality of images of the viewing region 24V. The number of images that are acquired may be user-defined. The analog to digital converter 120 converts the electrical signals from the photodetector 62 representative of the image to arrays of digital values. The digital values are stored in the image memory 130 as a plurality of images. The plurality of images are frame-averaged by the processor 140 to form a frame-averaged background image which is stored in the image memory 130. The background image is subtracted from subsequent digital images of the viewing region to create the normalized image. The background image may be periodically updated using a background correction function. Alternately, the operator may manually command the software to collect a new group of images from which to compute a new background image, or the operator may select a time interval for automatically computing a new background image.

As the next step of the method, an amplitude threshold is applied to the normalized image by the processor 140 to detect objects in the fluid stream F. The threshold may be visually selected by displaying an image intensity histogram on the display device 110D. The user may position two vertical cursors on this histogram to visually input the threshold value(s). Typically, there can be six threshold methods used: "In Range", "Out of Range", "Less than", "Greater than", "Less than or equal to", "Greater than or Equal to".

Next, an object-size histogram is generated by the image processor 140, stored in the results memory 150, and displayed on the associated display 110D. After every subsequent image is acquired the information displayed may be updated. The rate at which the display is updated may be controlled by a user input. The display unit 110D shows the total number of objects found so far in a given data collection interval, as well as the histogram of their sizes. After a user definable number of images have been collected the data may be recorded to a disk file, as determined by the user, and then the previous histogram may be redisplayed in a distinctive fashion and new histogram display may be initiated to provide the operator an indication of the frequency and sizes of the objects being detected.

Optionally a pixel intensity histogram may be shown in a separate window on the display 110D and may be updated after every incoming image. The pixel intensity histogram is useful for focusing the detected image on the image plane 60. A mean pixel intensity value may be calculated and displayed to monitor the output of the light source.

An erosion/dilation process may be optionally employed after the threshold step to remove from the image so-called "speckle" noise introduced by the optical detection system. Detected entities in the image, known as "blobs", are processed using the erosion/dilation technique. Although the extent of erosion/dilation may be user defined, in practice one cycle of erosion/dilation has been found to be adequate. The erosion/dilation technique finds connected groups of pixels which might be considered a candidate object in a fluid stream. The blob analysis generates a value representing the area of the candidate object. This value is compared to user-defined criteria for object size. The results of the comparison are reported and displayed in combination with the image and histogram already displayed.

Figure 12:
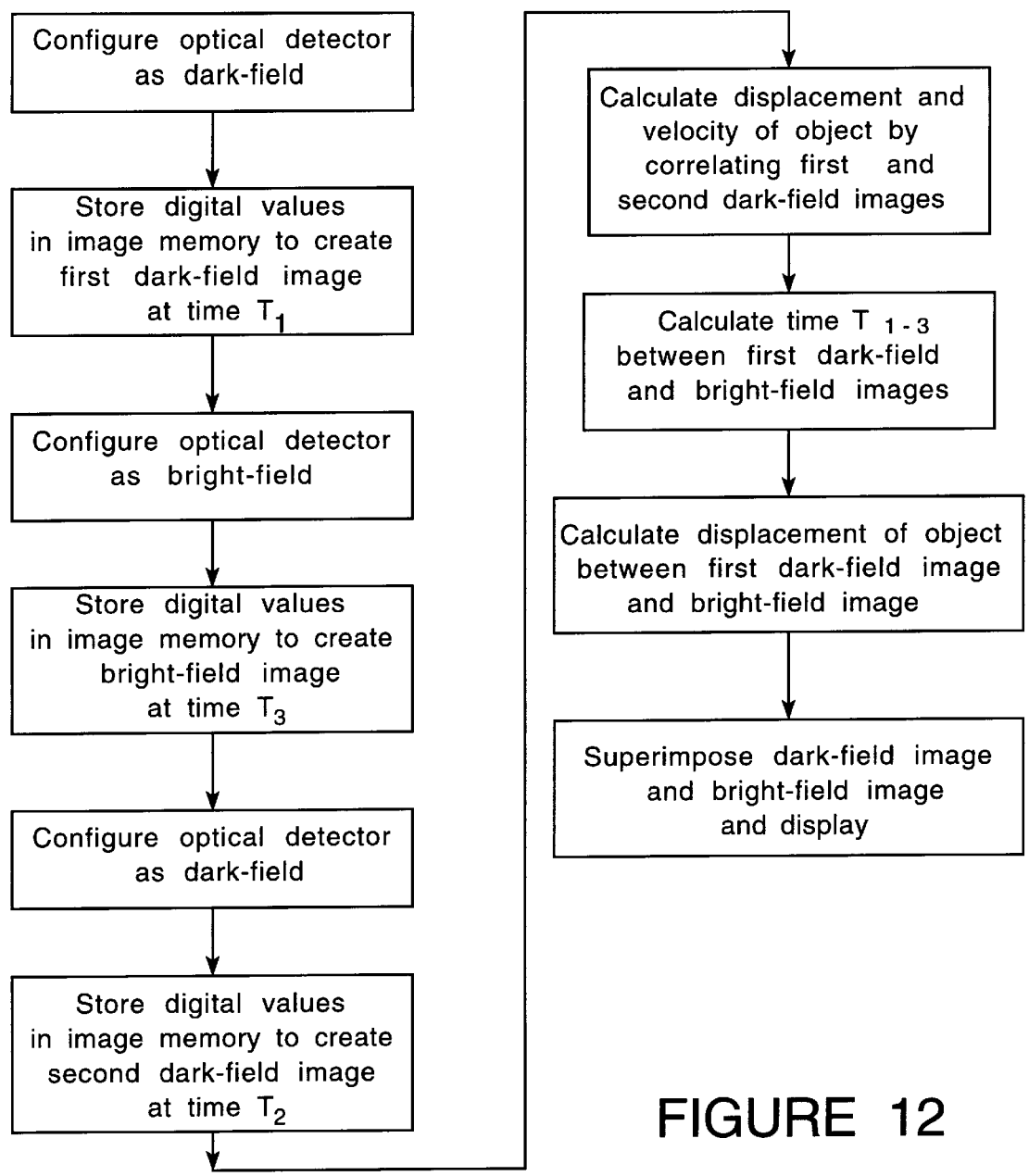
FIG. 12 is a block diagram illustrating the image processing method of the optical detection system of FIG. 10 for processing sequential bright-field and dark-field images.

The block diagram in FIG. 12 illustrates subsequent steps of the method applicable to sequentially-acquired bright-field and dark-field images of an object. With the optical detector assembly 50 of the optical probe 10 being configured in either the dark-field or bright-field optical arrangement, a first image of an object is produced at a first imaging time $T_1$ and a second image of the object is produced at a second imaging time $T_2$. Both images are stored in the image memory 130.

At a time $T_3$ intermediate the respective first and second imaging times $T_1$, $T_2$ an image of the same object in the viewing region 24V is produced with the optical detector assembly 50 of the optical probe 10 configured as the other of the optical arrangements. This intermediate image is also stored in the image memory 130. Using the first and second images and the first and second times, both the displacement and the velocity of the object within the viewing zone are calculated. The displacement of the object may be determined by correlating the first and second images using well known image correlation techniques.

For example, to correlate the first and second images the lateral displacement in the viewing region 24V of the object between the first and second images is calculated by iteratively shifting the first image in the flow direction and correlating the first and second images, until a maximum correlation is found. The time interval $T_{1-2}$ between the first and second images is calculated and the velocity $V_O$ of the object is calculated by dividing the displacement by the time interval. The time interval $T_{1-3}$ between the first and intermediate images is calculated. The lateral displacement between the object in the viewing region 24V of the first and intermediate images is calculated by multiplying the time interval $T_{1-3}$ by the object velocity $V_O$. The intermediate image may then be superimposed over one of the first or second images. Since the same object has been imaged in both the dark-field and the bright-field arrangements, the nature of the object in the images may be identified.

Either the dark-field optical arrangement or the bright-field optical arrangement may be used to produce the first and second images. Use of the dark-field optical arrangement for this purpose is preferred.

Exemplary Implementations

In use, the most common configuration of the probe apparatus of the present invention disposes the optical source assembly 30 and the optical detector assembly 50 in similarly sized housings 30H, 50H. The housings are installed diametrically opposite one another in the flow cell 22 or other location.

Of course, other mechanical configuration may be used. One such alternate configuration, known as a "shuttle probe", houses both the optical source assembly 30 and the optical detector assembly 50 in a single cylindrical housing. This cylindrical housing is equipped with the necessary seals to permit the optical components to slide into and out of the fluid stream without the necessity of interrupting the production process.

When the present invention is utilized in a high temperature environment, such as a polymer process, light is preferably delivered to the optical source assembly 30 via a fiber optic bundle able to withstand the high temperatures in polymer systems, such as one commercially available from Schott Fiber Optics, Inc. of Southbridge, Mass. In such an environment light is conveyed from the image plane 60 (or 80) to the photodetector 62 (or 82) by an optical image transmitting conduit such as an image transmitting fiber optic light pipe, also commercially available from Schott Fiber Optics, Inc.

The photodetector CCD array camera typically produces a standard RS-170 video signal which is transmitted to the analog to digital converter 120, which may be part of a image acquisition module installed in the computer 100. A module known as the "Meteor" available from Matrox of Dorval, Quebec, Canada, has been found suitable, although various other similar modules from other manufacturers could be used.

The image processing software of FIG. 11 may be implemented using a software package known as Labview™, available from National Instruments, of Austin, Tex., as a graphical user interface (GUI) and the Matrox Image Processing Library (MIL) to control the image acquisition module and to process the acquired images. The interface between these two software packages may be implemented using Visual C++ available from Microsoft, Inc. Redmond, Wash., which may also be used to implement additional image processing algorithms.

Applications

The present invention may be used for many gel sensing applications in the polymer processing industry. Some specific examples are described in this section.

Filter Performance Analysis

In applications where gel particles cause product performance problems, such as in the production of polymer films, in-line filters are employed to remove the gels from the flow stream. The filters become loaded after some period of time and gels and other particles begin to pass through. The present invention can be of great assistance in detecting when filters become ineffective and when filter changes are required. Considerable savings are possible if filters are changed at the most effective time.

Polymer Quality Analysis

Polymer quality can be analyzed in either on-line situations or off-line situations using the present invention. In on-line situations the polymer can be monitored ahead of the filtering equipment. In a typical off-line situation an extruder may be used to extrude samples of polymer pellets through a flow cell for measurement of the gel content using the present invention. Such a measurement technique has been found to be considerably more accurate than prior art manual gel counting techniques.

Extruder Mixing and Dynamics Measurements

The present invention may be employed to measure extruder performance. Parameters such as residence time distribution and mixing performance of various extruder screw configurations may be measured. Replacing the photodetector with a spectrophotometer, such as one manufactured by Ocean Optics of Dunedin, Fla., provides the capability of measuring mixing of dyed components in an extruder.

The optical source assembly may also be fitted with a bifurcated fiber optic bundle. In such a configuration the first leg of the bifurcated bundle supplies light to the viewing region and the second leg conveys light to the optical detector assembly so that a reflective measurement can be made. This allows a retroreflective version of the present invention to be implemented which avoids the necessity of diametrically opposed source and detector assemblies.

Those skilled in the art, having the benefit of the teachings of the present invention as hereinabove set forth, may impart numerous modifications thereto. Such modifications are to be construed as encompassed within the scope of the present invention as defined by the appended claims.

What is claimed is:

1. An imaging apparatus for imaging a viewing region, the apparatus including a collection of optical elements arranged in a predetermined sequence along both a first and a second optical path and cooperable to define a dark-field optical arrangement along the first path and a bright-field optical arrangement along the second path, the improvement comprising:

an optical element which receives light from the viewing region and directs and passes the light from the viewing region simultaneously to both the dark-field optical arrangement and the bright-field optical arrangement, so that a dark-field image of the viewing region is imaged onto a first image plane and a bright-field image of the viewing region is imaged onto a second image plane.

2. The apparatus of claim 1 wherein the optical element comprises a beam splitter.

3. The apparatus of claim 1 wherein the optical element comprises a reflective beam stop disposed in the dark-field optical arrangement which reflects light to the bright-field optical arrangement.

4. An optical probe capable of detecting in a fluid stream moving through a viewing region both an object detectable by a bright-field optical arrangement and an object detectable by a dark-field optical arrangement, said probe comprising:

an optical source assembly having a light source, a plate having an aperture therein, the aperture having a predetermined shape for defining a beam of light, and a lens arrangement for projecting the beam of light into the viewing region to illuminate the same;

an optical detector assembly including a first lens arrangement, a spatial filter, and a second lens arrangement, the spatial filter corresponding in size and shape to the aperture in the optical source assembly, the first lens arrangement focusing the illuminated portion of the viewing region onto the spatial filter to create a spatially filtered image of the viewing region, and the second lens arrangement focusing the spatially filtered image onto an image plane;

an actuator for positioning at least one of the aperture plate or the spatial filter into predetermined first and second positions with respect to each other, wherein, when in the first position the spatial filter and the aperture in the aperture plate are substantially aligned and when in the second position the spatial filter and the aperture in the aperture plate are substantially misaligned; so that when in the first position, only light from a dark-field-detectable object in a fluid moving through the viewing region is imaged onto the image plane while light from a bright-field-detectable object is substantially attenuated by the spatial filter, and when in the second position, substantially all the light illuminating the viewing region is imaged onto the image plane.

5. The apparatus of claim 4 wherein the shape of the spatial filter is the inverse of the shape of the aperture.

6. The apparatus of claim 4 wherein the spatial filter comprises a beam stop.

7. The apparatus of claim 4 wherein the spatial filter has a predetermined optical density profile.

8. The apparatus of claim 4 wherein the aperture is shaped as a transparent slit and the spatial filter is shaped as an opaque line and the aperture and spatial filter are rotationally aligned in the first position and are rotationally misaligned in the second position to define a predetermined azimuthal angle with respect to each other.

9. The apparatus of claim 8 wherein said azimuthal angle in the second position is in the range from about thirty (30) degrees to about one hundred fifty (150) degrees.

10. The apparatus of claim 8 wherein said azimuthal angle in the second position is about ninety (90) degrees.

11. The apparatus of claim 4 wherein the aperture and spatial filter are aligned in the first position and are translationally misaligned in the second position.

12. The apparatus of claim 4 further comprising a photodetector responsive to light imaged at the image plane.

13. The apparatus of claim 12, wherein the photodetector comprises a CCD device having an array of photodetecting sites which each generate an electrical signal representative of the intensity of the detected light on a corresponding picture element of the image plane.

14. An optical detection system comprising the apparatus of claim 13 and further comprising: a computer controlled image acquisition and processing system comprising: an analog to digital converter, an image memory, an image processor, a stored program memory, a results memory for storing image processor output results, an output port and associated display and printing means.

15. The apparatus of claim 4 wherein the light source is a pulsed source having a pulse duration sufficiently short so that images of moving objects are not blurred.

16. The apparatus of claim 15 further comprising a photodetector having an array of photodetecting sites which each generate an electrical signal representative of the intensity of the detected light on a corresponding picture element of the image plane, wherein the pulse duration of the light source is such that the smallest detectable object does not move more than one half of one picture element while illuminated.

17. The apparatus of claim 4 further comprising:
a housing, the housing having a channel extending therethrough, the channel having the viewing region therein, the channel having a central axis therethrough;
wherein the cross-sectional area of the channel is substantially constant.

18. An optical probe capable of simultaneously detecting in a fluid stream moving through a viewing region both an object detectable by a bright-field optical arrangement and an object detectable by a dark-field optical arrangement, said probe comprising:
an optical source assembly having a light source, a plate having an aperture therein, the aperture having a predetermined shape for defining a beam of light, and a lens arrangement for projecting the beam of light into the viewing region to illuminate the same;
an optical detector assembly including a first lens arrangement, a reflective beam stop, a second lens arrangement, and a third lens arrangement, the beam stop corresponding in size and shape to the aperture in the optical source assembly, the first lens arrangement focusing the illuminated portion of the viewing region onto the beam stop to create both a bright-field spatially filtered image and a dark-field spatially filtered image of the viewing region, the second lens arrangement focusing the bright-field spatially filtered image reflected by the beam stop onto a first image plane, the third lens arrangement focusing the dark-field spatially filtered image onto a second image plane, so that:
light from a bright-field-detectable object in a fluid moving through the viewing region is imaged onto the first image plane, and
light from a dark-field-detectable object in a fluid moving through the viewing region is imaged onto the second image plane.

19. A method for detecting an object in a fluid stream using the system of claim 14, wherein
the electrical signals from the photodetector are converted to digital values by the analog to digital converter to form a digital image of the viewing region, and
the digital image of the viewing region is stored in the image memory,
wherein the method comprises the steps of:
a) creating a normalized image of the viewing region by
i) acquiring a plurality of images of the viewing region,
ii) forming a frame-averaged background image from the plurality of images, and
iii) subtracting the background image from the digital image of the viewing region,
b) applying an amplitude threshold to the normalized image to detect objects in the fluid stream;
c) generating an object-size histogram,
d) storing the object-size histogram in the results memory, and
e) displaying the object-size histogram.

20. The method of claim 19 further comprising the steps of:
f) with the optical detector assembly of the optical probe being configured as one of the optical arrangements, producing a first and a second image of an object in accordance with that optical arrangement at respective first and second times and storing the first and second images,
g) with the optical detector assembly of the optical probe being configured as the other of the optical arrangements, producing an image of the same object in accordance with that other optical arrangement at a time intermediate said first and second times and storing the intermediate image,
h) using the first and second images and the first and second times, calculating both the displacement and the velocity of the object within the viewing zone, and
i) superimposing the intermediate image over one of the first and second images, thereby to identify the nature of the object in the images.

* * * * *